US012596113B2

(12) United States Patent
Bräutigam et al.

(10) Patent No.: US 12,596,113 B2
(45) Date of Patent: Apr. 7, 2026

(54) METHOD AND DEVICE FOR CHEMICAL-FREE DETERMINATION OF THE CHEMICAL OXYGEN DEMAND (CSB) IN AQUEOUS SAMPLES

(71) Applicant: Friedrich-Schiller-Universitaet Jena, Jena (DE)

(72) Inventors: Patrick Bräutigam, Jena (DE); Sascha Raufeisen, Berlin (DE); Michael Stelter, Chemnitz (DE); Samira Lambertz, Jena (DE)

(73) Assignee: FRIEDRICH-SCHILLER-UNIVERSITAET JENA, Jena (DE)

( * ) Notice: Subject to any disclaimer, the term of this patent is extended or adjusted under 35 U.S.C. 154(b) by 680 days.

(21) Appl. No.: 17/756,873

(22) PCT Filed: Dec. 3, 2020

(86) PCT No.: PCT/DE2020/101022
§ 371 (c)(1),
(2) Date: Nov. 17, 2022

(87) PCT Pub. No.: WO2021/110215
PCT Pub. Date: Jun. 10, 2021

(65) Prior Publication Data
US 2023/0068003 A1     Mar. 2, 2023

(30) Foreign Application Priority Data
Dec. 4, 2019    (DE) .......................... 102019008574.4

(51) Int. Cl.
| | |
|---|---|
| *G01N 33/18* | (2006.01) |
| *B01D 19/00* | (2006.01) |
| *G01N 27/416* | (2006.01) |

(52) U.S. Cl.
CPC ..... *G01N 33/1806* (2013.01); *B01D 19/0078* (2013.01); *G01N 27/4163* (2013.01); *G01N 27/4166* (2013.01)

(58) Field of Classification Search
CPC ........... G01N 33/1806; G01N 27/4163; G01N 27/4166; B01D 19/0078
See application file for complete search history.

(56) References Cited

U.S. PATENT DOCUMENTS

| | | | | |
|---|---|---|---|---|
| 6,875,337 | B1* | 4/2005 | Schrøder ................ | G01N 27/48 205/789.5 |
| 2010/0163430 | A1* | 7/2010 | Hall ........................ | G01N 27/26 205/775 |

FOREIGN PATENT DOCUMENTS

| | | | | |
|---|---|---|---|---|
| EP | 282441 | A2 | 9/1988 | |
| EP | 0834739 | A2 * | 4/1998 | ............. G01N 33/18 |

(Continued)

OTHER PUBLICATIONS

EPO machine-generated English language translation of Einaga et al. WO 2013/100101 A1 , patent published Jul. 4, 2013 (Year: 2013).*

(Continued)

*Primary Examiner* — Alexander S Noguerola

(74) *Attorney, Agent, or Firm* — Abel Schillinger, LLP

(57) ABSTRACT

The present invention relates to a method and a device for the chemical-free determination of the chemical oxygen demand (CODs) in aqueous samples. The object of the invention, to develop a method that compensates for the disadvantages of the standard method and at the same time is at least as good as this, in that it can determine the COD quickly and with a high measurement frequency without chemicals and is cheap and has a low personnel requirement and should be simple to automate, is achieved in that the chemical oxygen demand of aqueous samples is determined (Continued)

Figure 1:
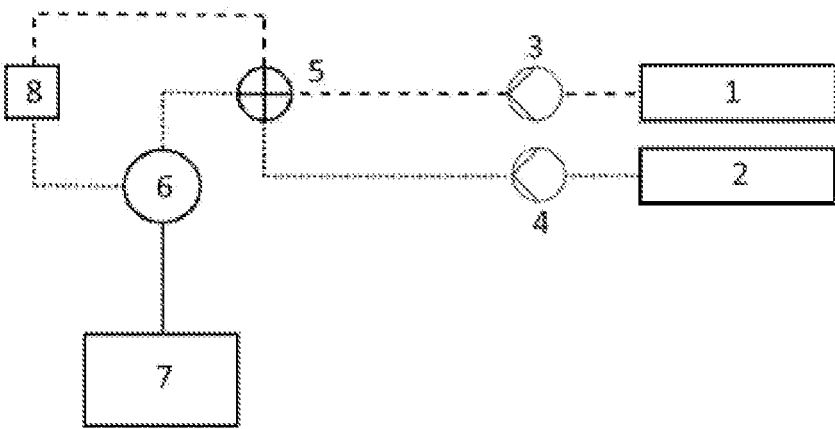

by non-specific oxidation of water components at an electrode (11), assisted by (ultra)sound from a sound source (15) in a frequency range in which no significant quantities of oxidative species are formed, i.e. below the cavitation threshold.

10 Claims, 2 Drawing Sheets

(56)                    References Cited

FOREIGN PATENT DOCUMENTS

KR              101208190  B1      12/2012
WO      WO 2013/100101  A1  *    7/2013    ............. G01N 33/18

OTHER PUBLICATIONS

EPO machine-generated English language translation of Henning Christiansen EP 0834739 A2, patent published Apr. 8, 1998 (Year: 1998).*

Jun Wang et al. "Ultrasound electrochemical determination of chemical oxygen demand using boron-doped diamond electrode", Electrochemistry Comm UN/Cations, Elsevier Amsterdam, NL, vol. 18, Feb. 10, 2012 (Feb. 10, 2012), pp. 51-54.

Goldenwall. "Ultrasonic Homogenizer Operation Instruction" Sep. 10, 2019 (Sep. 2019), pp. 1-10.

Dietrich Matz et al. "Degradation of endocrine disruptor bisphenol A by ultrasound-assisted electrochemical oxidation in water" Ulrasonics Sonochemistry, Butterworth-Heinemann, GB, vol. 39, May 30, 2017 (May 30, 2017), pp. 741-749.

Hielscher. "UP200S | UP400S Instruction manual" Jan. 10, 2007, Retrieved from the Internet: http://www.bendarygroup.com/images/instruction_manual_up200_400s_2007_ultrasonics.pdf.

Canals Antonio et al. "Ultrasound-assisted method for determination of chemical 1-10 oxygen demand" Analytical and Bioanalytical Chemistry, DE, vol. 374, No. 6, Oct. 25, 2002 (Oct. 25, 2002), pp. 1132-1140, Retrieved from the Internet: http://link.springer.com/article/10.1007/s00216-00 2-1578-2/fulltext.html.

Yang Bo et al. "Effective ultrasound electrochemical degradation of biological toxicity 1-10 and refractory cephalosporin pharmaceutical wastewater" Chemical Engeneering Journal, Elsevier, Amsterdam, NL, vol. 287, Dec. 1, 2015 (Dec. 1, 2015), pp. 30-37.

Canals A et al. New ultrasound assisted chemical oxygen demand determination 1-10 Ultrasonics Sonochemistry, Butterworth-Heinemann, GB, vol. 9, No. 3, Jul. 2002 (Jul. 2002), pp. 143-149.

H. B. Yu, H. Wang, X. Quan, S. Chen, Y. B. Zhang, Electrochem Commun 2007, 9, 2280-2285.

J. Wang, K. Li, H. B. Zhang, Q. Wang, Y. L. Wang, C. Yang, Q. B. Guo, J.P. Jia, Res Chern Intermediat 2012, 38, 2285-2294.

H. B. Yu, C. J. Ma, X. Quan, S. Chen, H. M. Zhao, Environ Sci Technol 2009, 43, 1935-1939.

* cited by examiner

METHOD AND DEVICE FOR CHEMICAL-FREE DETERMINATION OF THE CHEMICAL OXYGEN DEMAND (CSB) IN AQUEOUS SAMPLES

The present invention relates to a method and a device for the chemical-free determination of the chemical oxygen demand (COD) in aqueous samples.

The chemical oxygen demand (COD) is an important parameter for determining water quality. This is used to determine how much organic matter is contained in a water sample. The COD is an important parameter and can be found in many laws, including those regarding water monitoring and wastewater discharge, and can decide, among other things, whether wastewater can be discharged into surface water. The amount of oxygen required for aeration in the sewage treatment plant also depends on this, which is why the parameter can in principle be used for control purposes in the sewage treatment plant. The examination of water samples both at the inlet and at the outlet of the sewage treatment plant can be used for this.

The standard method for determining the COD specified by the DIN standard is based on the oxidation of a water sample with potassium dichromate under strongly sulfated conditions. The method has some inherent disadvantages. For example, large quantities of toxic and environmentally harmful ($K_2Cr_2O_7$, $HgSO_4$) and corrosive (concentrated $H_2SO_4$ (9.8 M)) chemicals have to be used. Long analysis times (2-4 h) mean that real-time analysis cannot be carried out and the method is therefore not suitable for process control. Trained personnel are required for the analysis, and automation is difficult. Operating costs are high due to the need for chemicals, disposal of toxic waste, and personnel.

Some alternative methods for determining COD have been developed to compensate for the disadvantages of the standard method.

An electrochemical method for determining the COD is described in EP 282441 A2. This method is based on the non-specific oxidation of the organic water components at a lead dioxide working electrode. In this process, reactive species such as OH radicals and ozone are formed at this electrode, which non-specifically oxidize water components with a need for oxygen. The measured current is proportional to the COD.

The disadvantage of lead dioxide electrodes is that toxic lead compounds can be dissolved by the chemical and mechanical stress and possibly get into the environment. Also, the linear working ranges achieved with this method are smaller than those of the standard method, so that it cannot replace it.

An example of a non-toxic electrode that can be used to determine COD is the boron-doped diamond (BDD) electrode. This was first used by Yu et al. (H. B. Yu, H. Wang, X. Quan, S. Chen, Y. B. Zhang, Electrochem Commun 2007, 9, 2280-2285) in an amperometric sensor to determine the COD. The sensor works according to the same principle as the sensor with lead dioxide electrodes. The detection limit achieved with it is higher than that of the standard method. Even the linear working range does not cover low COD values. The investigation is done in batch, so it is difficult to automate.

One way to improve the electrochemical method is to introduce sound or ultrasound. The interaction between sound and electrochemistry for the oxidation of organic pollutants has already been investigated in various publications. Dietrich et al. (M. Dietrich, M. Franke, M. Stelter, P. Braeutigam, Ultrason Sonochem 2017, 39, 741-749)

describe that the rate of the electrochemical reaction can be increased by ultrasound. This happens through an increased mass transport and a reduced diffusion layer.

This can be used in the electrochemical COD determination to increase the measurement signal and thus reduce the detection limit of the method. In addition, the measurement time is reduced because a constant signal is established more quickly.

When sound is used to determine the COD, it should be noted that oxidative species can also arise in the process. If these lead to the degradation of organic pollutants, the measurement result can be falsified. For a reliable method for determining the COD, this must be avoided.

Wang et al. (J. Wang, K. Li, H. B. Zhang, Q Wang, Y. L. Wang, C. Yang, Q. B. Guo, J. P. Jia, Res Chem Intermediat 2012, 38, 2285-2294) use ultrasound in a batch setup with a frequency of 20 kHz and a power of 60 W in combination with BDD electrodes. With this setup, the linear working range was increased. Further improvements of the method could not be reported. In this publication, only ultrasound with a frequency of 20 kHz and a power of 850 W/cm$^2$ was introduced—an operating point at which the formation of additional reactive oxidative species is to be expected (M. Dietrich, M. Franke, M. Stelter, P. Braeutigam, Ultrason Sonochem 2017, 39, 741-749). However, the influence of the ultrasound on the degradation of the pollutants was not considered.

Another disadvantage of the standard method is that it cannot be used for an automated measurement with a high measurement frequency. The new method should be able to determine the COD at a high measurement frequency in order to be able to use it to control municipal and industrial sewage treatment plants, for example.

In Yu et al. (H. B. Yu, C. J. Ma, X. Quan, S. Chen, H. M. Zhao, Environ Sci Technol 2009, 43, 1935-1939) a measurement cell with a BDD electrode for the continuous determination of the COD was presented. However, only a small linear working range could be achieved here, which is below that of the standard method.

The aim of the invention is to develop a method and a device that compensates for the disadvantages of the standard method and at the same time is at least as good as the latter. This could not be achieved in any of the existing inventions. The method should be able to determine the COD without chemicals, quickly and with a high measurement frequency. It should be cheap, require little in the way of human resources and be easy to automate. Furthermore, a wide linear working range and a low detection limit are desirable.

This object is to be achieved by an electrochemical measurement cell with a working electrode that is able to oxidize organic water components without discrimination. The determination is to be supported by the use of (ultra) sound. In order to achieve automation and the highest possible measurement frequency, the measurement should take place in a cell through which the flow occurs.

The invention relates to a method and a device for the electrochemical determination of the chemical oxygen demand of a liquid sample, in particular a water or wastewater sample.

The measurement is to take place in a three-electrode arrangement wherein the working electrode is an electrode capable of non-selectively oxidizing organic substances. For this, it must have a high overpotential for oxygen development. In addition, it should have a low background current in the corresponding voltage range.

The functional principle of this method is that a high potential for the oxidation of the water components with an oxygen requirement is applied without the competitive reaction of the oxygen formation having an influence on the measurement. Examples of such electrodes are PbO2 and BDD.

In the three-electrode arrangement used, a reference electrode and a counter electrode are used in addition to the working electrode.

The voltage is regulated between the working electrode and the reference electrode. For this purpose, the reference electrode is operated with as little current as possible in order to avoid overvoltage effects. A type 2 electrode is used as the reference electrode, the potential of which is independent of the electrolyte. Examples of possible reference electrodes are the silver-silver chloride electrode and the calomel electrode.

The current is measured at the counter electrode. For this purpose, an electrode is used that has a larger area than the working electrode, so that the flowing current is limited only by the conversion at the working electrode. In addition, the counter electrode should have a high overvoltage for the decomposition of water. Possible materials for counter electrodes are, for example, titanium, platinum or boron-doped diamond.

Furthermore, the measurement cell must contain an electrolyte solution. This must have a certain conductivity in order to make the electrochemical measurement possible.

Various electrochemical methods can be used to determine the concentration of the oxidizable components in the water sample, in particular the COD.

With the amperometric method, a constant voltage is applied between the working and reference electrodes. The constant voltage applied should be in a range in which reactive species, for example OH radicals, are generated at the working electrode. These reactive species are responsible for a non-discriminatory oxidation of all water components that require oxygen. By measurement of the current flowing between the working and counter electrodes, conclusions can be drawn about the material turnover and thus the concentration of the oxidizable substances contained in the sample.

Another possibility is the complete oxidation of all water components with a need for oxygen at a constant voltage (coulometric method). This method measures the total charge flowing until the sample is completely oxidized. The measured charge is directly dependent on the COD of the sample.

Other methods are based on applying a linearly increasing or a cyclically increasing and decreasing potential. With these voltammetric methods, the current-voltage curve is recorded. By comparing the recorded current-voltage curve with the measurement curve of an electrolyte solution without adding a sample, conclusions can be drawn about the COD of the sample.

The measurement signal is evaluated by comparing the measured value with a calibration curve. This must be determined by measuring standard samples and saved for later use. Alternatively, a calibration-free determination can be made using the coulometric measurement.

In this embodiment, a main component of the electrochemical cell is the (ultra)sound source.

The (ultra)sound is intended to improve the mass transport of the oxidizable water components to the electrode and reduce the diffusion layer. This increases the current and the measurement signal rises. The measurement range in which the COD can be determined then increases. Furthermore, establishment of equilibrium is accelerated and the measuring time is reduced.

When ultrasound is used during the measurement, the organic water components can also be broken down. This decomposition does not take place quantitatively and cannot be recorded by the electrochemical measurement, so that the measured value is falsified. For this reason, the (ultra)sound parameters must be selected in such a way that the measurement is optimized, but no degradation of the organic load takes place. For this purpose, a range is selected in which no (significant quantities) of oxidative species are formed solely by the ultrasound, which would falsify the measurement signal at the electrode. This can be monitored by targeted control of the amplitude used on the sound generator. A frequency between 8 kHz and 50 MHz, preferably 100 kHz and 20 MHz, should be used for measuring the COD in the non-cavitation range. The intensity of the sound generator must be adjusted so that cavitation does not occur. In addition to the frequency, the temperature and the amount of dissolved gas have an influence on the intensity to be set. Accordingly, the intensity to be set for the specified frequency range is a maximum of $1 \ W/cm^2$. Other parameters to consider are the distance between the sound source and the electrode and the arrangement of these in relation to each other, which determines whether the ultrasound hits the electrode directly or indirectly.

The sound is also useful for reactivating the electrodes. The oxidation of certain organic substances on the electrode surface can lead to the formation of polymer layers that reduce the active surface area of the electrode. The electrode surfaces can be cleaned by the use (ultra)sound in the cavitation range. If this reactivation is repeated regularly, this leads to a measurement signal that is stable in the long term. In addition, the service life of the sensors can be increased and costs reduced by reducing maintenance work. For cleaning, it is desirable to already exceed the cavitation threshold by low intensities. Frequencies of 8 kHz to 50 MHz, preferably 8 kHz to 2 MHz, particularly preferably 8 kHz to 80 kHz, are therefore used, at which the cavitation threshold can already be exceeded by $0.1 \ W/cm^2$.

In order to be able to use the (ultra)sound both to support the measurement and for activation, it should be modulable, i.e. it should be able to cover wide amplitude ranges. Alternatively, two sound sources (of different frequencies) could be used to support the measurement on the one hand (sub-cavitation range) or to keep the electrode surface active (cavitation range).

In addition, the sound can serve to degas the electrolyte and sample solution. The gas bubbles contained in the solution and formed during the reaction can collect in front of the electrode, especially in the case of a flow cell arrangement. The electrode surface is thereby reduced, which can lead to a reduction in the current and in particular to a reduction in reproducibility. In a suitable arrangement, the sound input can ensure that the gas is removed from the solution and thus increase reproducibility.

The arrangement of the electrodes and the sound source should in particular take place in a cell through which flow occurs. This makes it easy to automate the method, which expands its range of application. In order to make this possible, pumps are used to convey the electrolyte or sample solution and valves are used to switch between the solutions.

The COD determination is performed using a setup that includes at least the following items:

a working electrode that can non-selectively oxidize organic water components without high background currents, a reference electrode and a counter electrode, a means of setting and measuring current and voltage, usually in the form of a potentiostat, a unit for evaluating and storing the measured values, a modulable sound source, pumps, autosamplers, mixing chambers to control the flow of electrolyte and sample solution through the electrochemical cell.

EXEMPLARY EMBODIMENT

The subject matter of the invention is explained below with reference to figures, without the subject matter of the invention being restricted thereby.

A possible setup is shown in FIG. 1.

FIG. 1: Basic setup of a device for determining the COD.

Figure 2:
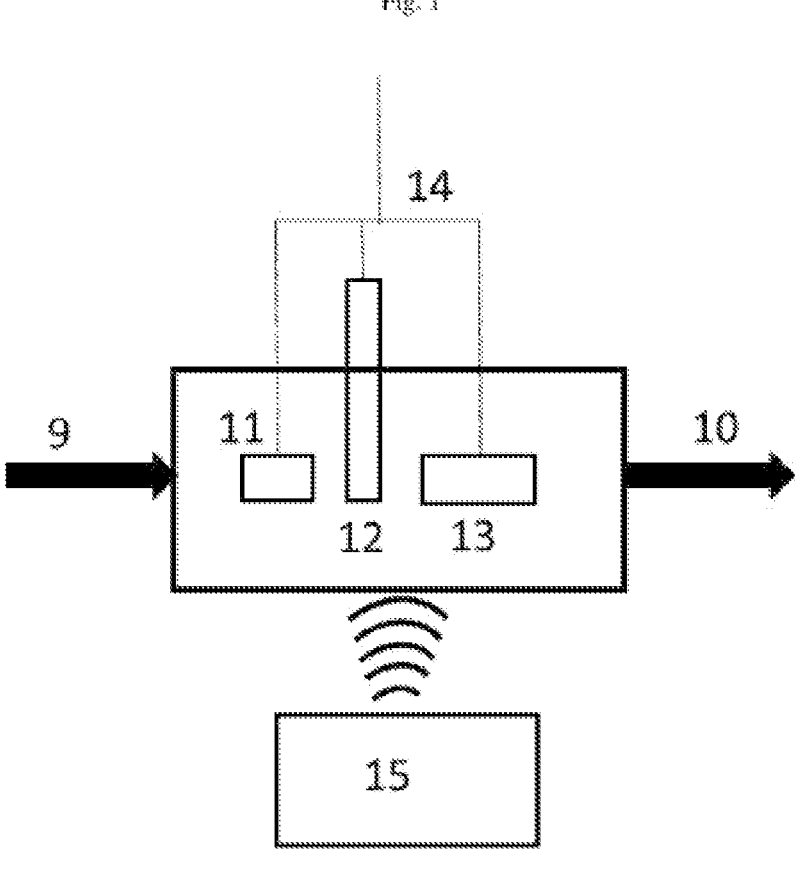

FIG. 2: Basic setup of the electrochemical measurement cell.

Figure 3:
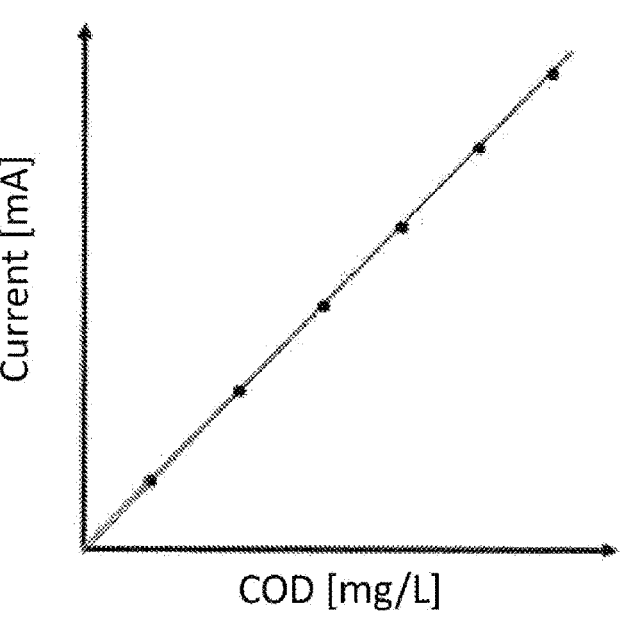

FIG. 3: Calibration of the method for determining the COD.

Figure 4:
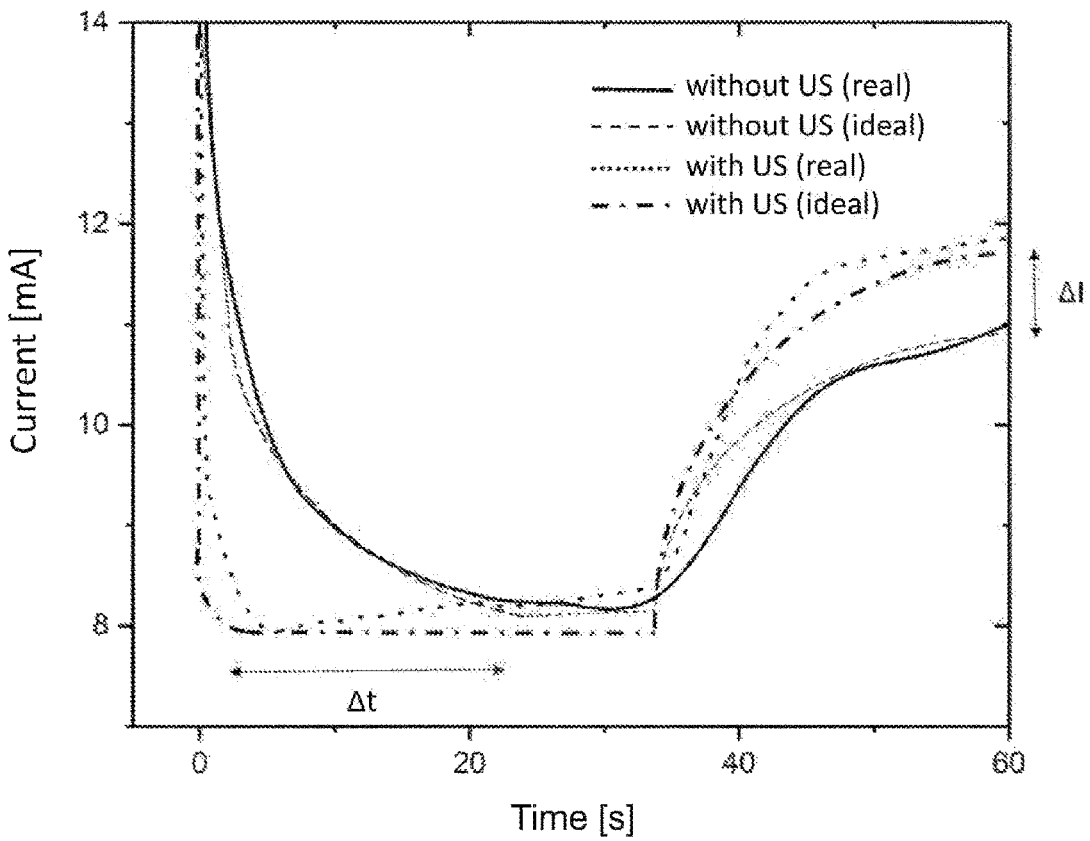

FIG. 4: Improvement of the current signal through the use of ultrasound.

The device for determining the chemical oxygen demand shown in FIG. 1 contains the electrochemical measurement cell 6, which is described in more detail in FIG. 2. With the help of pumps 3 and 4, the sample solution 1 and the electrolyte solution 2 are pumped through the cell.

In this embodiment, there is an inlet for the electrolyte and an inlet for the sample solution. The valve 5 can be used to switch between the two flows so that first, the electrolyte flows into the electrochemical cell and the sample flows past it. This is shown in FIG. 1 by the differently marked lines. After a lead time, the valve 5 is then switched so that the sample now flows through the cell and the electrolyte flows past it. The sample must be dissolved in an electrolyte solution in order to have sufficient conductivity. After passing through the cell, the solutions flow into the waste container 8. There is also a measuring and control unit 7 for current and voltage. A potentiostat, for example, is used for this purpose.

FIG. 2 shows the electrochemical cell in more detail. Inlet 9 and outlet 10 for the solutions are shown here. The three-electrode arrangement consists of a boron-doped diamond electrode as the working electrode 11, the reference electrode 12 and the counter electrode 13. The three electrodes are connected to the measuring and control unit 7 via the contacts 14. A sound source 15 is also indicated symbolically.

In this embodiment, the amperometric method described above is used. A BDD electrode is used as the working electrode 11. 0.001 M $Na_2SO_4$ with 0.001 M $H_2SO_4$ is used as the electrolyte. An ultrasonic bath is used as the sound source 15. This introduces ultrasound at a frequency of 35 kHz and a power of 0.3 $W/cm^2$ into the cell, whereby no cavitation is generated. A voltage of 2.8 V is applied. First the electrolyte flows through the measurement cell. A constant background current has been established after 30 s. The switch is made to the sample flow. Measurements are continued for a further 1 minute so that a constant current can be established again. The COD can be determined from the difference between the sample current and the background current. The current signal shows a linear dependence on the COD of the sample. By calibrating the method with standard samples of known COD, the COD can then be determined from the measured current signal. Such a calibration is shown in FIG. 3.

The current difference can be increased by introduction of ultrasound into the measurement cell, as shown in FIG. 4. Here, the current-time curves measured in the experiment were supplemented with curves representing the ideal progression. In principle, a current-time curve for the investigated amperometric method runs in such a way that after application of the voltage at 0 s, the current initially falls sharply and then, after a certain time, a state of equilibrium with a constant current is reached. After the change to the sample solution after 30 s, the current increases sharply due to the oxidation. A constant current is also restored after a waiting period. The difference between the investigations with and without ultrasound is that, firstly, the background current is established more quickly after the voltage is applied, which means that the measurement can be shortened. In the example shown, one could switch from the electrolyte to the sample solution after just 5 s and would thus reduce the measurement by 25 s to 65 s. Secondly, the signal current is higher in the case of the ultrasound-supported measurement, which lowers the detection limit of the measurement. In the example shown, the current difference increases by 30%, which means that the detection limit could be reduced from 10 mg/L to 7 mg/L.

When the coulometric method is used, the charge that flows until a sample is completely oxidized is measured instead of the current. The COD can be calculated directly from the charge. No calibration is necessary here.

LIST OF REFERENCE NUMERALS

1 Sample solution
2 Electrolyte solution
3 Pump
4 Pump
5 Valve
6 Measurement cell
7 Measuring and control unit
8 Waste container
9 Inlet
10 Outlet
11 Working electrode
12 Reference electrode
13 Counter electrode
14 Contacts
15 (Ultra)sound source

The invention claimed is:

1. A method for determining the chemical oxygen demand of an aqueous sample (1) comprising: conducting non-specific oxidation of water components at an electrode (11), wherein the non-specific oxidation is supported by ultrasound from a sound source (15) in a power and frequency range below a cavitation threshold, wherein the frequency is at least 35 kHz.

2. The method according to claim 1, comprising using a three-electrode arrangement with a working electrode (11), a counter electrode (13) and a reference electrode (12).

3. The method according to claim 1, comprising determining the chemical oxygen demand from a current strength measured during the oxidation of the water components by comparison with a calibration.

4. The method according to claim 1, characterized in that the chemical oxygen demand is determined from a charge which flowed during complete oxidation.

5. The method according to claim 1, comprising applying a linearly increasing or a linearly increasing and decreasing potential and obtaining the chemical oxygen demand from a difference between a current-voltage line obtained during the measurement and of a corresponding electrolyte solution (2) not containing the aqueous sample.

6. The method according to claim 1, comprising operating the sound source (15) during the measurement of the chemical oxygen demand in a frequency range from 35 kHz to 20 MHz, and at a power below the cavitation threshold.

7. The method according to claim 6, comprising operating the sound source (15) for cleaning in a frequency range of 8 kHz to 50 MHz and at a power above the cavitation threshold.

8. The method according to claim 1, comprising arranging electrodes (11, 12 and/or 13) and the sound source (15) in a flow cell.

9. The method according to claim 8, comprising additionally using the sound for degassing an electrolyte (2) and a sample solution (1).

10. A device for determining chemical oxygen demand of a sample solution, comprising:

a working electrode (11), a counter electrode (13), and a reference electrode (12) in a three-electrode circuit, an electrolyte, a control unit for measuring and controlling a potential between the working electrode (11) and the reference electrode (12), or for measuring and controlling a current between the working electrode (11) and the counter electrode (13), one or more ultrasound sources (15) for activating different powers and one or more pumps (3, 4) for transporting the electrolyte (2) and the sample solution (1).

\* \* \* \* \*